United States Patent [19]
Winter et al.

[11] Patent Number: 5,892,083
[45] Date of Patent: Apr. 6, 1999

[54] ORGANOMETALLIC SOURCE COMPOUNDS FOR CHEMICAL VAPOR DEPOSITION

[75] Inventors: Charles H. Winter, Bloomfield; Jennifer L. Sebestl, Pointe Park, both of Mich.

[73] Assignee: Wayne State University, Detroit, Mich.

[21] Appl. No.: 982,196

[22] Filed: Dec. 1, 1997

[51] Int. Cl.$^6$ ....................................................... C07F 7/10
[52] U.S. Cl. ............................................ 556/412; 564/511
[58] Field of Search ........................... 260/665 R, 665 G, 260/665 B; 556/404, 412, 511

[56] References Cited

PUBLICATIONS

CA:120:66309 abs of JP05136063, Jun. 1993.
CA:84:43488 abs of "Chemistry of N–aryl–substituted metal amides VII" Froehlich, Z Chem, 15(8), pp. 316–317, 1975.
CA:115:84156 abs of "The synthesis of bis(hexamethyldisilylamido) barium(II)", Boncella, Polyhedron, 10(7), pp. 769–770, 1991.
CA:115220101 abs of "Synthesis and Chemistry of the bis(trimethylsilyl) amido bis tetra hydrofuranates of Group 2 metals magnesium ,calcium , strontium and barium", Bradley, Polyhedron, 9 (24), pp. 2959–2964, 1990.

Inorg Chem, Gindelberger "Preparation and Properties of Mg, Ca, Sr, and Ba Selenolates and Tellurolates". 33, pp. 6293–6299, Dec. 1994.

CA: 121:314489 abs of Gindelberger's Inorganic chem paper 33(26) pp. 6293–6299, Dec. 1994.

CA:126:126085 abs of "1,3–Bis (trimethylsilyl)–2–phenyl–1–aza–3–phosphapropenide Anions as Bidentate Ligands", Westerhausen, Inor Chem, 36(4) pp. 521–527, Feb. 1997.

*Primary Examiner*—Gary Geist
*Assistant Examiner*—Jean F. Vollano
*Attorney, Agent, or Firm*—Brooks & Kushman P.C.

[57] ABSTRACT

Compounds of the formula $$M(XR_2)L_n$$

where M is a Group IIa metal, X is an azogen, R is a hydrocarbyl or silyl group, L is a neutral azogen-containing donor ligand, and n=1 or 2 have good low temperature volatility and can be used as Group IIa metal MOCVD precursors.

15 Claims, No Drawings

ORGANOMETALLIC SOURCE COMPOUNDS FOR CHEMICAL VAPOR DEPOSITION

TECHNOLOGICAL FIELD

The present invention pertains to organometallic Group IIa metal compounds, particularly organomagnesium compounds suitable for use in chemical vapor deposition processes.

BACKGROUND OF THE INVENTION

Numerous technologies require the uniform deposition of a variety of metals from the vapor phase in controlled amounts. One such technology is the preparation of light-emitting diodes and other photonic devices by the doping of Group 13 nitrides by magnesium. Magnesium doping of GaN devices is theoretically capable of providing stable, high-luminosity blue and green photonic devices. Magnesium is particularly useful as a dopant due to its low diffusion constant in semiconductor matrices, its desirable acceptor energy level, and the relatively low toxicity of its compounds.

Thus far, the magnesium sources used in such techniques as metal organic chemical vapor deposition (MOCVD), chemical beam epitaxy (CBE), and related techniques have employed bis(cyclopentadienyl)magnesium ($Cp_2Mg$) and substituted derivatives. However, $Cp_2Mg$ is a solid of high melting point and low vapor pressure. Moreover, the cyclopentadienyl ligands of $Cp_2Mg$ are known to bond strongly to metals, their cleavage from which are relatively high energy processes. The low vapor pressure and low reactivity of $Cp_2Mg$ and like compounds cause a so-called "memory effect" during growth of doped films, where $Cp_2Mg$ adheres to the walls of the reactor, only to slowly desorb following cessation of dopant precursor flow. This process temporarily lowers dopant concentration initially, and prolongs dopant availability following the desired end point. Thus, a broad, rather than an abrupt doping profile is created. The memory effect places a severe impediment on the preparation of devices with well defined doping profiles.

Despite the known inadequacies of $Cp_2Mg$ as a dopant source, only very few attempts have been reported to alleviate such problems. Hatano et al., APPL. PHYS. LETT., 1991, 58, 1488 have employed $Mg(Al(CH_3)_4)_2$ to prepare doped $Ga_xAl_{1-x}As$ films at high doping levels and with flat doping profiles, thus exhibiting virtually no memory effect. However, the presence of Al and the facile reversion of this compound to the constituent metal alkyls prevents its use for magnesium doping.

CVD precursors for depositing Group IIa metal are disclosed in related U.S. Pat. Nos. 5,280,012; 5,225,561; and 5,453,494. Calcium, barium, and strontium precursors of the bis(cyclopentadienyl) or acetylacetonate-type complexed with a mono- or multidentate ligand are disclosed for use in preparing doped copper oxide superconductors. However, no magnesium precursors are exemplified, and the Group IIa complexes prepared exhibited relatively high sublimation temperatures, higher than $Cp_2Mg$.

It would be desirable to provide Group IIa metal-containing, and particularly magnesium-containing organic source compounds having high volatility which can be used as MOCVD precursors. It would further be desirable to provide magnesium MOCVD precursors which exhibit little or no memory effect.

SUMMARY OF THE INVENTION

It has now been surprisingly discovered that certain three- and four-coordinate magnesium bis(amides) and their Group Va analogs containing one or two neutral, Group Va-containing donor ligands may be sublimed at relatively low temperatures to serve as magnesium dopants in the preparation of magnesium doped films. Analogous Group IIa bis(amides) may serve as low temperature volatile precursors for deposition of Ca, Ba, and Sr.

DESCRIPTION OF THE PREFERRED EMBODIMENTS

The organometallic precursor compounds of the present invention correspond to the formula:

$$M(XR_2)_2L_n$$

wherein M is a Group IIa metal, preferably magnesium; X is N, P, or As; R is a hydrocarbon or silyl radical, for example, an optionally substituted and optionally aliphatically unsaturated alkyl, aryl, cycloalkyl, aralkyl, alkaryl, or $Si(R^1)_3$ radical, where $R^1$ may be a substituted or unsubstituted, optionally aliphatically unsaturated alkyl, aryl, cycloalkyl, alkaryl, or aralkyl; L is a neutral donor ligand containing N, P, or As as the electron donor atom; and wherein n is 1 or 2. Most preferably, the subject invention precursors are magnesium precursors corresponding to the formula:

$$Mg(NR_2)_2L_n$$

where R, L, and n are defined as above. Preferably, the precursors may be sublimed at 0.1 torr at temperatures lower than 130° C.

The bis(amides) and their phosphorus and organic analogs may be the same or different, and preferably comprise units having relatively bulky R substituents. The R and $R^1$ substituents may be alkyl substituents such as methyl, ethyl, n-propyl, isopropyl, n-butyl, isobutyl, t-butyl, 2-ethylhexyl, octyl, decyl, octadecyl, 2,2,4-trimethylpentyl, and the like, preferably $C_1$–$C_{30}$ alkyl groups and more preferably $C_4$–$C_{20}$ alkyl groups; cycloalkyl groups such as cyclopropyl, cyclobutyl, cyclopentyl, cyclohexyl, cycloheptyl, cyclooctyl, cyclododecyl, methylcyclopentyl, methylcyclohexyl, dimethylcyclohexyl, and the like, preferably $C_5$–$C_{20}$ cycloalkyl groups; aryl groups such as phenyl, naphthyl, anthracenyl, methylphenyl, dimethylphenyl, methylnaphthyl, dimethylnaphthyl, and the like, preferably $C_6$–$C_{14}$ aryl ring systems optionally substituted with alkyl, alkenyl, cycloalkyl or like groups; aralkyl groups such as benzyl and 1,1-dimethylbenzyl; and silyl groups such as trimethylsilyl, triethylsilyl, triphenylsilyl, methyldiethylsilyl, and the like.

The various alkyl, cycloalkyl, aryl, and arylalkyl R and $R^1$ groups may be substituted with substituents which do not interfere with precursor synthesis or use as a magnesium or other Group IIa metal source precursor. Suitable substituents include alkyl groups, particularly $C_{1-8}$ alkyl groups and cycloalkyl groups, aryl groups, particularly $C_6$ and $C_{10}$ aryl groups, halogens, particularly chlorine and fluorine, most particularly the latter; alkoxy groups, preferably $C_{1-8}$ alkoxy, most preferably methoxy and ethoxy groups; nitro groups, cyano groups, and silyl groups. By the term "substituted" as used herein with respect to the various R and $R^1$ groups is meant an alkyl, cycloalkyl, etc. group which is substituted in such manner that a stable precursor of the foregoing formulae may be prepared.

The various R groups may also contain aliphatic unsaturation, i.e. alkenyl, cycloalkenyl, or alkynyl unsaturation. The term "optionally unsaturated" as used herein relative to R and $R^1$ refers to unsaturated alkyl, cycloalkyl, alkylsilyl, etc. groups having one or more sites of aliphatic unsaturation, or to aryl, alkaryl, or aralkyl groups substituted with an unsaturated aliphatic hydrocarbon group.

The metal M may be magnesium, calcium, barium, or strontium, but is preferably magnesium. Each M is bis (amidized), amidization referring in this case to analogous phosphorus and arsenic derivatives as well. Hereinafter, the class of nitrogen, phosphorus, and arsenic will be collectively termed "azogens". Amide groups and their phosphorus and arsenic analogs will be termed "azogenamides". Although each azogenamide group may be a distinct chemical entity, e.g., —$NR_2$, the two amide groups may also be linked through one or more common R or $R^1$ groups, e.g.,

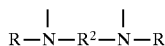

where each R is the same or different, and $R^2$ is a divalent hydrocarbon or hydrocarbonsilyl linking group analogous to the definitions previously set forth for monovalent R and $R^1$ groups. However, in the case of an $R^2$ azogenamide linking group, the length of the carbon chain must be such that both azogenamide groups may assume the proper steric position in the Group IIa metal coordination sphere. Thus, $R^2$ must contain minimally two carbon atoms, and may not be a single, planar ring structure of 6 atoms or less.

Dimeric, oligomeric and polymeric bis(azogenamides) may be prepared through use of one azogenamide-forming molecule with bis(azogen) functionality. An example of such a compound is one corresponding to the formula:

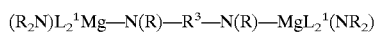

where each Mg is bound through an amide linkage to $R_2N$ and is coordinated with, in this example, two donor ligands $L^1$, the second amide linkage provided by linkage to the secondary nitrogens —NR—, commonly linked through divalent linking group $R^3$ which may be a divalent hydrocarbon corresponding to R or $R^1$, etc.

The ligands L are monodentate neutral ligands containing an azogen, preferably N, as an electron pair donor. Non-limiting examples of ligands which are suitable are aromatic heterocyclic compounds containing a single ring nitrogen or two ring nitrogens, separated, in the latter case preferably by at least two carbon atoms. Analogous phosphorus and arsenic compounds may also be used. When the ring contains two ring azogens, the potential for dimeric, oligomeric, or polymeric precursors arises. Such precursors may be useful provided that their vapor pressures and reactivities are high enough to be used as precursors. An example of a dimeric precursor formula is:

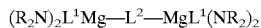

where $L^1$ is a single azogen containing donor and $L^2$ contains two azogen donors. Preferable neutral donor ligands are pyridine, quinoline, isoquinoline, acridine, 1,4-oxazine, and like compounds, optionally substituted by $C_{1-20}$ alkyl, $C_{5-12}$ cycloalkyl, and $C_{6-10}$ aryl groups. Most preferably, the donor ligands are 2-picoline or 2,3,5-collidine. Suitable donor ligands containing 2 ring nitrogens are pyrazine and pyrido[4,3-b]pyridine. Single nitrogen-containing donor ligands are preferred. Other azogen donor atoms are also contemplated.

The Group IIa precursor compounds may be prepared by any suitable method. Preferably, however, the precursors are prepared by the room temperature ligand exchange of nitrogen or azogen donor ligands with a Group IIa metal bis (amide) (or its azogen analog) ligand complex. The ligand to be exchanged may be a single bidentate ligand or may be two monodentate ligands. The ligands added by exchange must not displace the bis(azogenamide) moieties from the starting metal bis(azogenamide) ligand complex.

The reaction may take place neat, in solution, or when appropriate, in the gas phase. Reaction in solution is preferred. Suitable solvents include aromatic solvents such as benzene and toluene, and hydrocarbon solvents such as hexane. Other organic solvents may be used as well. The reaction temperature may range from well below zero to significantly above room temperature. Room temperature reaction is preferred, however. The reaction may take place under an inert gas or nitrogen blanket or in air, and may be conducted at any convenient pressure. Precursors obtained containing two donor ligands (n=2) can be sublimed in vacuuo to produce three-coordinate metal complexes containing but one ligand (n=1).

Precursors where n=2 may be converted to precursors where n=1 through loss of one neutral donor ligand. This conversion may be accomplished simply by heating the $L_2$-containing precursor, preferably at reduced pressure, as illustrated in Examples 3 and 4. Moreover, this conversion is reversible, as shown by Example 5. The facile interconversion of the mono-neutral donor ligand species and bis-neutral donor ligand species presents further synthetic routes to each species. For example, a bis-neutral donor ligand species may be synthesized by the process disclosed in the subject invention or by other synthetic methods and converted to the corresponding mono-neutral ligand donor species. Similarly, a mono-neutral ligand donor species may be synthesized and converted to the corresponding bis-neutral ligand donor species. The two ligands L need not be the same. It is believed that the magnesium-containing mono-neutral ligand donor species is the first neutral three-coordinate magnesium compound thus far reported.

Having generally described this invention, a further understanding can be obtained by reference to certain specific examples which are provided herein for purposes of illustration only and are not intended to be limiting unless otherwise specified.

EXAMPLE 1

Bis(bis(trimethylsilyl)amido)bis(2,3,5-collidine) magnesium

A 100-mL Schlenk flask was charged with bis(bis (trimethylsilyl)amido)bis(tetrahydrofuran)-magnesium (0.200 g, 0.460 mmol), a magnetic stir bar, and benzene (40 mL). 2,3,5-collidine (0.12 g, 0.91 mmol) was then added to this solution. The mixture was stirred for 18 h at room temperature. The volatile components were removed at reduced pressure to afford a yellow-orange solid. This solid was extracted into hexane (10 mL) and the resultant solution was filtered through a 2-cm pad of Celite®. The filtrate was cooled to –20° C. for 18 h to afford colorless blocks of 1 (0.18 g, 66%).

Spectroscopic and analytical data for 1: mp 72°–73° C.; IR (Nujol, $cm^{-1}$) 1249 (s), 1211 (m), 1148 (m), 1021 (s), 973 (s), 887 (s), 841 (s), 782 (s), 738 (s), 725 (s), 661 (s), 610 (s), 537 (s); $^1H$ NMR ($C_6D_6$, δ) 8.39 (s, 2,3,5-collidine C-H), 6.63 (s, 2,3,5-collidine C-H), 2.43 (s, 2,3,5-collidine $CH_3$), 1.81 (s, 2,3,5-collidine $CH_3$), 1.69 (s, 2,3,5-collidine $CH_3$), 0.33 (s, $Si(CH_3)_3$); $^{13}C\{^1H\}$ NMR ($C_6D_6$, ppm) 154.32 (s, 2,3,5-collidine C-$CH_3$), 147.00 (s, 2,3,5-collidine C-H), 139.41 (s, 2,3,5-collidine C-H), 132.00 (s, 2,3,5-collidine C-CH$_3$), 131.26 (s, 2,3,5-collidine C-CH$_3$), 22.04 (s, 2,3,5-collidine C-CH$_3$), 18.62 (s, 2,3,5-collidine C-CH$_3$), 17.45 (s, 2,3,5-collidine C-CH$_3$), 5.87 (s, Si (CH$_3$)$_3$); Anal. Calcd for C$_{28}$H$_{58}$MgN$_4$Si$_4$: C, 57.25; H, 9.95; N, 9.54. Found: C, 56.25; H, 10.00; N, 9.61.

EXAMPLE 2

Bis(bis(trimethylsilyl)amido)bis(2-picoline) magnesium

In a fashion similar to the preparation of Example 1, bis(bis(trimethylsilyl)amido)bis(tetrahydrofuran)-magnesium (0.200 g, 0.460 mmol) and 2-picoline (0.085 g, 0.91 mmol) were reacted in benzene (40 mL) to afford 2 as a pale orange solid (0.169 g, 70%). Complex 2 was extremely soluble in hexane and would not crystallize, even after extended cooling of concentration solutions at −20° C. Accordingly, it could not be purified further from this solvent.

Spectroscopic and analytical data for 2: mp 103°–105° C.; IR (Nujol, cm$^{-1}$) 1277 (m), 1242 (s), 1160 (m), 1109 (m), 1061 (m), 1007 (s), 894 (s), 875 (s), 824 (s), 791 (s), 763 (s), 750 (s), 728 (m), 667 (s), 648 (m), 635 (m), 611 (s); $^1$H NMR (C$_6$D$_6$, δ) 8.58 (broad d, 3- or 6-H of 2-picoline), 6.71 (t, J=7.8 Hz, 4- or 5-H of 2-picoline), 6.37 (broad t, J=6.9 Hz, 4- or 5-H of 2-picoline), 6.28 (broad d, 3- or 6-H of 2-picoline), 2.47 (s, CH$_3$ of 2-picoline), 0.30 (s, Si(CH$_3$)$_3$); $^{13}$C{$^1$H} NMR (C$_6$D$_6$, ppm) 158.41 (s, 2-C of 2-picoline), 148.88 (s, C-H of 2-picoline), 139.52 (s, C-H of 2-picoline), 125.50 (s, C-H of 2-picoline), 121.94 (s, C-H of 2-picoline), 24.10 (s, C-CH$_3$ of 2-picoline), 5.86 (s, Si(CH$_3$)$_3$); Anal. Calcd for C$_{24}$H$_{50}$MgN$_4$Si$_4$: C, 54.25; H, 9.49; N, 10.54. Found: C, 45.58; H, 9.63; N, 8.79.

EXAMPLE 3

Bis(bis(trimethylsilyl)amido)(2,3,5-collidine) magnesium

Sublimation of 1 (1.951 g, 3.321 mmol) at 90° C. (0.1 mmHg) in a one-inch glass tube using a horizontal tube furnace afforded colorless blocks of 3 (0.816 g, 53%).

Spectroscopic and analytical data for 3: mp 94° C.; IR (Nujol, cm$^{-1}$) 1241 (s), 1004(s), 931 (w), 893 (m), 873 (s), 839 (s), 824 (s), 789 (w), 747 (m), 665 (m), 610 (m); $^1$H NMR (C$_6$D$_6$, δ) 8.47 (s, 2,3,5-collidine C-H), 6.53 (s, 2,3,5-collidine C-H), 2.45 (s, 2,3,5-collidine CH$_3$), 1.74 (s, 2,3,5-collidine CH$_3$), 1.56 (s, 2,3,5-collidine CH$_3$), 0.34 (s, Si(CH$_3$)$_3$); $^{13}$C{$^1$H} NMR (C$_6$D$_6$, ppm) 154.21 (s, 2,3,5-collidine C-CH$_3$), 146.54 (s, 2,3,5-collidine C-H), 141.56 (s, 2,3,5-collidine C-CH$_3$), 133.74 (s, 2,3,5-collidine C-H), 132.49 (s, 2,3,5-collidine C-CH$_3$), 21.80 (s, 2,3,5-collidine C-CH$_3$), 18.46 (s, 2,3,5-collidine C-CH$_3$), 17.23 (s, 2,3,5-collidine C-CH$_3$), 5.86 (s, N(Si(CH$_3$)$_3$)$_2$). Anal. Calcd for C$_{20}$H$_{47}$MgN$_3$Si$_4$: C, 51.52; H, 10.16; N, 9.01. Found: C, 48.10; H, 9.85; N, 8.49.

EXAMPLE 4

Bis(bis(trimethylsilyl)amido)(2-picoline)magnesium

Sublimation of 2 (0.366 g, 0.689 mmol) at 115° C. (0.1 mmHg) in a one-inch glass tube using a horizontal tube furnace afforded colorless blocks of 4 (0.138 g, 46%).

Spectroscopic and analytical data for 4: mp 110°–111° C.; IR (Nujol, cm$^{-1}$) 1305 (m), 1277 (m), 1242 (s), 1160 (m), 1061 (m), 999 (s), 894 (s), 875 (s), 826 (m), 793 (s), 763 (s), 750 (s), 728 (m), 667 (s), 648 (m), 635 (m), 611 (m); $^1$H NMR (C$_6$D$_6$, δ) 8.57 (broad d, 3- or 6-H of 2-picoline), 6.73 (t, J=7.8 Hz, 4- or 5-H of 2-picoline), 6.38 (broad t, J=6.6 Hz, 4- or 5-H of 2-picoline), 6.30 (broad d, 3- or 6-H of 2-picoline), 2.47 (S, CH$_3$ of 2-picoline), 0.31 (s, Si(CH$_3$)$_3$); $^{13}$C{$^1$H} NMR (C$_6$D$_6$, ppm) 158.41 (s, 2-C of 2-picoline), 148.84 (s, C-H of 2-picoline), 139.68 (s, C-H of 2-picoline), 125.60 (s, C-H of 2-picoline), 122.02 (s, C-H of 2-picoline), 24.05 (s, C-CH$_3$ of 2-picoline), 5.84 (s, Si (CH$_3$)$_3$); Anal. Calcd for C$_{18}$H$_{43}$MgN$_3$Si$_4$: C, 49.34; H, 9.89; N, 9.59. Found: C, 47.64; H, 9.74; N 9.31. Carbon microanalyses were consistently low, apparently due to formation of magnesium carbide upon combustion. For a discussion of this problem, see: Westerhausen, M.; Digeser, M. H.; Schwartz, W. INORG. CHEM., 1997, 36, 521.

EXAMPLE 5

Reaction Of 3 With 2,3,5-Collidine To Afford 1

A 100-mL Schlenk flask was charged with 3 (0.245 g, 0.525 mmol), 2,3,5-collidine (0.0749 mL, 0.578 mmol), hexane (30 mL), and a stir bar. The reaction mixture was stirred for 18 h at 23° C., and the flask was then placed in a −20° C. freezer. After 48 h, crystals of 1 were isolated (0.141 g, 46%). The $^1$H and $^{13}$C{$^1$H} NMR spectra of 1 isolated in this way were identical to those of material prepared as described above.

EXAMPLE 6

Crystallization Of 3 From Hexane

A 100-mL Schlenk flask was charged with 3 (0.320 g, 0.686 mmol) and hexane (10 mL). The flask was then placed in a −20° C. freezer. After one week, crystals of 1 were isolated (0.028 g, 14%). The $^1$H and $^{13}$C{$^1$H} NMR spectra of 1 isolated in this way were identical to those of material prepared as described above.

The bis-(neutral donor ligand) and mono-(neutral donor ligand) complexes represent extremely promising source compounds for doping semiconductor films. Compounds 3 and 4 are substantially more volatile than Cp$_2$Mg which sublimes at 160° C. in the same apparatus used to sublime complexes 3 and 4. Complex 3 can easily be maintained in the liquid state for steady transport to a MOCVD apparatus in view of its low melting point of only 94° C. The complexes of the subject invention also exhibit considerably higher volatility than the starting bis(tetrahydrofuran) complexes. Complexes 3 and 4 may be sublimed at 90° C. and 115° C. (0.1 torr), respectively, while the corresponding bis(amide)bis(tetrahydrofuran) species and the bis(bis (trimethylsilyl)amido) magnesium dimer (Wannagat et al., ANGEW. CHEM., Int. Eng. Ed., 1963, 2, 47) both sublime at about 140° C. under the same conditions. Thus, the three-coordinate complexes 3 and 4 exhibit substantially more volatility than even closely related structures.

The structures of complexes 1 and 4 were determined by conventional x-ray techniques. Complex 1 crystallized as a distorted tetrahedral monomer, with N(1)—Mg—N(1) and N(2)—Mg—N(2) angles of 120.95° and 87.93°, respectively. The distortion is believed largely due to the bulky bis(trimethylsilyl)amido groups. The magnesium-nitrogen bond lengths were 2.0467 Å for the bis(trimethylsilyl)amido bond and 2.259 Å for the 2,3,5-collidine ligand.

Complex 4 crystallized with trigonal planar geometry with two bis(trimethylsilyl)amido ligands and one 2-picoline ligand. The sum of the angles about magnesium was 359.5, indicating near perfect planarity. The N(1)—Mg—N(2) bond angle was 137.3°, consistent with the bulky nature of the bis(trimethylsilyl)amido ligands. The plane of the 2-picoline ligand was approximately perpendicular to the plane of the three nitrogens. Magnesium-bis (trimethylsilyl)amido bond lengths were measured to be 1.969 and 1.959, while the Mg-2-picoline bond length was measured as 2.098 Å. These values are considerably shorter than the analogous values for 1, and reflect the diminished steric interactions and increased electronic unsaturation present in 4. The compounds described are suitable, in particular for preparing doped GaAs and GaN films.

Having now fully described the invention, it will be apparent to one of ordinary skill in the art that many changes and modifications can be made thereto without departing from the spirit or scope of the invention as set forth herein.

What is claimed is:

1. An organometallic compound having the formula:

wherein L is a nitrogen-containing neutral donor ligand, n is 1 or 2, and R is an optionally substituted and optionally aliphatically unsaturated alkyl, cycloalkyl, aryl, aralkyl, alkaryl or $R_3{}^1Si$ group wherein $R^1$ is an optionally substituted and optionally aliphatically unsaturated alkyl, cycloalkyl, aryl, alkaryl or aralkyl group, or where $R_2$ with N forms a cyclic non-aromatic structure.

2. The compound of claim 1 wherein $NR_2$ is bis(trimethylsilyl)amido.

3. The compound of claim 1 wherein L is selected from the group consisting of substituted pyridine ligands.

4. The compound of claim 3 wherein L is selected from the group consisting of 2,3,5-collidine, 2-picoline, and mixtures thereof.

5. The compound of claim 1 wherein n=2.

6. The compound of claim 1 wherein n=1.

7. The compound of claim 1 wherein said compound sublimes at 0.1 torr at a temperature less than about 130° C.

8. The compound of claim 1, wherein said compound sublimes at 0.1 torr at a temperature less than 160° C.

9. A process for depositing a magnesium metal-containing film on a substrate, said process comprising contacting said substrate maintained at an elevated temperature with a vapor produced by subliming a compound of claim 1, said elevated temperature sufficient to decompose said compound, depositing magnesium metal, wherein said compound sublimes at 0.1 torr at a temperature of less than 160° C.

10. A process for depositing a magnesium metal-containing film on a substrate, said process comprising contacting said substrate maintained at an elevated temperature with a vapor produced by subliming a compound of claim 2, said elevated temperature sufficient to decompose said compound, depositing magnesium metal. wherein said compound sublimes at 0.1 torr at a temperature of less than 160° C.

11. A process for depositing a magnesium metal-containing film on a substrate, said process comprising contacting said substrate maintained at an elevated temperature with a vapor produced by subliming a compound of claim 3, said elevated temperature sufficient to decompose said compound, depositing magnesium metal, wherein said compound sublimes at 0.1 torr at a temperature of less than 160° C.

12. A process for depositing a magnesium metal-containing film on a substrate, said process comprising contacting said substrate maintained at an elevated temperature with a vapor produced by subliming a compound of claim 4, said elevated temperature sufficient to decompose said compound, depositing magnesium metal, wherein said compound sublimes at 0.1 torr at a temperature of less than 160° C.

13. A process for depositing a magnesium metal-containing film on a substrate, said process comprising contacting said substrate maintained at an elevated temperature with a vapor produced by subliming a compound of claim 7, said elevated temperature sufficient to decompose said compound, depositing magnesium metal, wherein said compound sublimes at 0.1 torr at a temperature of less than 160° C.

14. A process for depositing a magnesium metal-containing film on a substrate, said process comprising contacting said substrate maintained at an elevated temperature with a vapor produced by subliming a compound of claim 6, said elevated temperature sufficient to decompose said compound, depositing magnesium metal, wherein said compound sublimes at 0.1 torr at a temperature of less than 160° C.

15. A process for depositing a magnesium metal-containing film on a substrate, said process comprising contacting said substrate maintained at an elevated temperature with a vapor produced by subliming a compound of claim 7, said elevated temperature sufficient to decompose said compound, depositing magnesium metal, wherein said compound sublimes at 0.1 torr at a temperature of less than 160° C.

* * * * *

UNITED STATES PATENT AND TRADEMARK OFFICE
CERTIFICATE OF CORRECTION

PATENT NO : 5,892,083
DATED : April 6, 1999
INVENTOR(S) : Charles H. Winter, et al.

It is certified that error appears in the above-identified patent and that said Letters Patent is hereby corrected as shown below:

Column 8, Line 27, Claim 13: delete "7" and insert --5--.

Signed and Sealed this

Twenty-eighth Day of September, 1999

Attest:

Q. TODD DICKINSON

*Attesting Officer*  *Acting Commissioner of Patents and Trademarks*